(12) United States Patent
Danger et al.

(10) Patent No.: US 11,479,817 B2
(45) Date of Patent: Oct. 25, 2022

(54) METHODS FOR DISCRIMINATING A TOLERANT SUBJECT

(71) Applicants: INSERM (Institut National de la Santé et de la Recherche Médicale), Paris (FR); Université de Nantes, Nantes (FR); Centre Hospitalier Universitaire de Nantes, Nantes (FR); Centre National de la Recherche Scientifique, Paris (FR)

(72) Inventors: Richard Danger, Nantes (FR); Sophie Brouard, Sucé-sur-Erdre (FR); Magali Giral, Nantes (FR); Gérard Ramstein, Mauves-sur-Loire (FR)

(73) Assignees: INSERM (Institut National de la Santé et de la Recherche Médicale, Paris (FR); Université de Nantes, Nantes (FR); Centre Hospitalier Universitaire de Nantes, Nantes (FR); Centre National de la Recherche Scientifique, Paris (FR)

( * ) Notice: Subject to any disclaimer, the term of this patent is extended or adjusted under 35 U.S.C. 154(b) by 907 days.

(21) Appl. No.: 16/319,264

(22) PCT Filed: Jul. 21, 2017

(86) PCT No.: PCT/EP2017/068517
§ 371 (c)(1),
(2) Date: Jan. 18, 2019

(87) PCT Pub. No.: WO2018/015551
PCT Pub. Date: Jan. 25, 2018

(65) Prior Publication Data
US 2019/0264281 A1  Aug. 29, 2019

(30) Foreign Application Priority Data
Jul. 22, 2016 (EP) .................... 16305948

(51) Int. Cl.
*C12Q 1/6876* (2018.01)
(52) U.S. Cl.
CPC ..... *C12Q 1/6876* (2013.01); *C12Q 2600/158* (2013.01)
(58) Field of Classification Search
CPC ............ C12Q 1/6876; C12Q 2600/158
See application file for complete search history.

(56) References Cited

U.S. PATENT DOCUMENTS

2010/0304996 A1\* 12/2010 Seyfert ............ G01N 33/56972
506/9

FOREIGN PATENT DOCUMENTS

| EP | 1 990 425 | 11/2008 |
|---|---|---|
| WO | WO 2010/136576 | 12/2010 |
| WO | WO 2011/068829 | 6/2011 |
| WO | WO 2011/138609 | 11/2011 |
| WO | WO 2016/075232 | 5/2016 |

OTHER PUBLICATIONS

Baron, et al. "A common gene signature across multiple studies relate biomarkers and functional regulation in tolerance to renal allograft." *Kidney International* 87, No. 5 (2015): 984-995.
Sagoo, et al. "Development of a cross-platform biomarker signature to detect renal transplant tolerance in humans." *The Journal of Clinical Investigation* 120, No. 6 (2010): 1848-1861.
Sarwal. "Fingerprints of transplant tolerance suggest opportunities for immunosuppression minimization." *Clinical Biochemistry* 49. No. 4-5 (2016): 404-410.
Viklicky, et al. "B-cell-related biomarkers of tolerance are up-regulated in rejection-free kidney transplant recipients." *Transplantation* 95, No. 1 (2013): 148-154.
Abramowicz et al., "Cyclosporine withdrawal from a mycophenolate mofetil-containing immunosuppressive regimen: results of a five-year, prospective, randomized study". J Am Soc Nephrol. Jul. 2005;16(7):2234-40.
Benitez et al., "Prospective multicenter clinical trial of immunosuppressive drug withdrawal in stable adult liver transplant recipients". Hepatology. Nov. 2013;58(5):1824-35.
Biais et al., "Clinical relevance of pulse pressure variations for predicting fluid responsiveness in mechanically ventilated intensive care unit patients: the grey zone approach". Crit Care. Nov. 4, 2014;18(6):587.
Braud et al., "Immunosuppressive drug-free operational immune tolerance in human kidney transplant recipients: Part I. Blood gene expression statistical analysis". J Cell Biochem. Apr. 15, 2008;103(6):1681-92.

(Continued)

*Primary Examiner* — Samuel C Woolwine
(74) *Attorney, Agent, or Firm* — Klarquist Sparkman, LLP

(57) ABSTRACT

The present invention relates to a method for discriminating an operationally tolerant (TOL) subject from a non-operationally tolerant (STA) subject, comprising the following steps:
i) establishing a composite score of tolerance (cSoT) with the expression levels of six genes in a biological sample obtained from said subject and two clinical parameters; wherein said six genes are ID3, AKR1C3, CD40, CTLA4, TCL1A and MZB1, and
wherein said cSoT is established by the following formula:

$$cSoT = \sum_i^n = \beta_i \times Exprs + \beta_{test\ time} \times age_{test\ time} +$$
$$\beta_{trans\ time} \times age_{trans\ time} + intercept - scaling\ coefficient$$

ii) comparing this cSoT with a predetermined reference value; and
iii) concluding that the subject is TOL when the cSoT is higher than the predetermined reference value or concluding that the subject is STA when the cSoT is lower than the predetermined reference value.

10 Claims, 3 Drawing Sheets

(56) References Cited

OTHER PUBLICATIONS

Braudeau et al., "Variation in numbers of CD4+CD25highFOXP3+ T cells with normal immuno-regulatory properties in long-term graft outcome". Transpl Int. Oct. 2007;20(10):845-55.
Braza et al., "Central role of CD45RA-Foxp3hi memory regulatory T cells in clinical kidney transplantation tolerance". J Am Soc Nephrol. Aug. 2015;26(8):1795-805.
Braza et al., "Reconsidering the bio-detection of tolerance in renal transplantation". Chimerism. Jan.-Mar. 2013;4(1):15-7.
Brouard et al., "Comparative transcriptional and phenotypic peripheral blood analysis of kidney recipients under cyclosporin A or sirolimus monotherapy". Am J Transplant. Dec. 2010;10(12):2604-14.
Brouard et al., "Identification of a gene expression profile associated with operational tolerance among a selected group of stable kidney transplant patients". Transpl Int. Jun. 2011;24(6):536-47.
Brouard et al., "Identification of a peripheral blood transcriptional biomarker panel associated with operational renal allograft tolerance". Proc Natl Acad Sci USA. Sep. 25, 2007;104(39):15448-53.
Brouard et al., "The natural history of clinical operational tolerance after kidney transplantation through twenty-seven cases". Am J Transplant. Dec. 2012;12(12):3296-307.
Chesneau et al., "Tolerant kidney transplant patients produce B cells with regulatory properties". J Am Soc Nephrol. Oct. 2015;26(10):2588-98.
Chesneau et al., "Unique B cell differentiation profile in tolerant kidney transplant patients". Am J Transplant. Jan. 2013;14(1):144-55.
Ciancio et al., "A randomized pilot study of donor stem cell infusion in living-related kidney transplant recipients receiving alemtuzumab". Transplantation. Nov. 15, 2013;96(9):800-6.
Danger et al., "Upregulation of miR-142-3p in peripheral blood mononuclear cells of operationally tolerant patients with a renal transplant". J Am Soc Nephrol. Apr. 2012;23(4):597-606.
Dantal et al., "Effect of long-term immunosuppression in kidney-graft recipients on cancer incidence: randomised comparison of two cyclosporin regimens". Lancet. Feb. 28, 1998;351(9103):623-8.
Dell'Oglio et al., "The anti-fibrotic effect of mycophenolic acid-induced neutral endopeptidase". J Am Soc Nephrol. Dec. 2010;21(12):2157-68.
Deng et al., "Noninvasive discrimination of rejection in cardiac allograft recipients using gene expression profiling". Am J Transplant. Jan. 2006;6(1):150-60.
Dugast et al., "Failure of calcineurin inhibitor (tacrolimus) weaning randomized trial in long-term stable kidney transplant recipients". Am J Transplant. Nov. 2016;16(11):3255-3261.
Erickson et al., "A cost analysis of tolerance induction for two-haplotype match kidney transplant recipients". Am J Transplant. Jan. 2016;16(1):371-3.
Everly et al., "Incidence and impact of de novo donor-specific alloantibody in primary renal allografts". Transplantation. Feb. 15, 2013;95(3):410-7.
Foucher et al., "A clinical scoring system highly predictive of long-term kidney graft survival". Kidney Int. Dec. 2010;78(12):1288-94.
Gautier et al., "affy—analysis of Affymetrix GeneChip data at the probe level". Bioinformatics. Feb. 12, 2004;20(3):307-15.
Heidt et al., "B cell markers of operational tolerance can discriminate acute kidney allograft rejection from stable graft function". Transplantation. May 2015;99(5):1058-1064.
Hricik et al., "Adverse outcomes of tacrolimus withdrawal in immune-quiescent kidney transplant recipients". J Am Soc Nephrol. Dec. 2015;26(12):3114-22.
Kawai et al., "Long-term results in recipients of combined HLA-mismatched kidney and bone marrow transplantation without maintenance immunosuppression". Am J Transplant. Jul. 2014;14(7):1599-611.
Krepsova et al., "Effect of induction therapy on the expression of molecular markers associated with rejection and tolerance". BMC Nephrol. Aug. 19, 2015;16:146.
Lakkis & Sayegh, "Memory T cells: a hurdle to immunologic tolerance". J Am Soc Nephrol. Sep. 2003;14(9):2402-10.
Lee et al., "Validation study of peripheral blood diagnostic test for acute rejection in kidney transplantation". Transplantation. Oct. 15, 2014;98(7):760-5.
Leventhal et al., "Genomic biomarkers correlate with HLA-identical renal transplant tolerance". J Am Soc Nephrol. Sep. 2013;24(9):1376-85.
Leventhal et al., "Nonchimeric HLA-identical renal transplant tolerance: regulatory immunophenotypic/genomic biomarkers". Am J Transplant. Jan. 2016;16(1):221-34.
Lozano et al., "Comparison of transcriptional and blood cell-phenotypic markers between operationally tolerant liver and kidney recipients". Am J Transplant. Sep. 2011;11(9):1916-26.
Massart et al., "The DESCARTES-Nantes survey of kidney transplant recipients displaying clinical operational tolerance identifies 35 new tolerant patients and 34 almost tolerant patients". Nephrol Dial Transplant. Jun. 2016;31(6):1002-13.
Mastoridis et al., "Biomarkers and immunopathology of tolerance". Curr Opin Organ Transplant. Feb. 2016;21(1):81-7.
Miller, "Cardiovascular toxicities of immunosuppressive agents". Am J Transplant. Oct. 2002;2(9):807-18.
Muller-Steinhardt et al., "The pharmacodynamic effect of sirolimus: individual variation of cytokine mRNA expression profiles in human whole blood samples". Immunobiology. 2009;214(1):17-26.
Newell et al., "Identification of a B cell signature associated with renal transplant tolerance in humans". J Clin Invest. Jun. 2010;120(6):1836-47.
Newell et al., "Longitudinal studies of a B cell-derived signature of tolerance in renal transplant recipients". Am J Transplant. Nov. 2015;15(11):2908-20.
Ojo et al., "Chronic renal failure after transplantation of a nonrenal organ". N Engl J Med. Sep. 4, 2003;349(10):931-40.
Pallier et al., "Patients with drug-free long-term graft function display increased numbers of peripheral B cells with a memory and inhibitory phenotype". Kidney Int. Sep. 2010;78(5):503-13.
Petrara et al., "Post-transplant lymphoproliferative disorders: from epidemiology to pathogenesis-driven treatment". Cancer Lett. Dec. 1, 2015;369(1):37-44.
Roedder et al., "A three-gene assay for monitoring immune quiescence in kidney transplantation". J Am Soc Nephrol. Aug. 2015;26(8):2042-53.
Roedder et al., "The kSORT assay to detect renal transplant patients at high risk for acute rejection: results of the multicenter AART study". PLoS Med. Nov. 11, 2014;11(11):e1001759.
Rohart, "Multiple hypotheses testing for variable selection". arXiv preprint arXiv:1106.3415, 2011.
Roussey-Kesler et al., "Clinical operational tolerance after kidney transplantation". Am J Transplant. Apr. 2006;6(4):736-46.
Sawinski et al., "Calcineurin inhibitor minimization, conversion, withdrawal, and avoidance strategies in renal transplantation: a systematic review and meta-analysis". Am J Transplant. Jul. 2016;16(7):2117-38.
Scandling et al., "Chimerism, graft survival, and withdrawal of immunosuppressive drugs in HLA matched and mismatched patients after living donor kidney and hematopoietic cell transplantation". Am J Transplant. Mar. 2015;15(3):695-704.
Scandling et al., "Tolerance and withdrawal of immunosuppressive drugs in patients given kidney and hematopoietic cell transplants". Am J Transplant. May 2012;12(5):1133-45.
Silva et al., "Preserving the B-cell compartment favors operational tolerance in human renal transplantation". Mol Med. Jul. 18, 2012;18:733-43.
Tullius et al., "The combination of donor and recipient age is critical in determining host immunoresponsiveness and renal transplant outcome". Ann Surg. Oct. 2010;252(4):662-74.

* cited by examiner

METHODS FOR DISCRIMINATING A TOLERANT SUBJECT

CROSS REFERENCE TO RELATED APPLICATIONS

This is the U.S. National Stage of International Application No. PCT/EP2017/068517, filed Jul. 21, 2017, which was published in English under PCT Article 21(2), which in turn claims the benefit of EP Application No. 16305948.8, filed Jul. 22, 2016.

FIELD OF INVENTION

The invention is in the field of transplantation, particularly, the invention allows to identify whether a subject is tolerant among the subjects treated with an immunosuppressive treatment.

BACKGROUND OF INVENTION

Solid-organ transplantation relies on the use of immunosuppressive treatment (IS) to prevent graft rejection. However, because of long-term IS side-effects, including cancers, cardiovascular diseases, infections and nephrotoxicity [1-3], physicians are encouraged to reduce IS exposition while still protecting the graft from immune aggression [4]. Ideally, achievement of allograft tolerance in solid-organ transplantation, i.e., allograft acceptance in absence of immunosuppression (IS) treatment, would be a tremendous insight by avoiding IS side-effects. This would also decrease cost of transplantation maintenance [5], reduce cases of re-transplantation while improving recipients' quality of life. In this aim, several protocols of tolerance induction have been attempted with successes, mainly through transient chimera establishment via bone marrow or stem cells transfer [6-10]. However, so far, effectiveness is limited to living donors or zero-mismatch deceased-donor and only few cases of successful tolerance induction with HLA mismatches have been reported [6, 11]. Interestingly, tolerance has also been observed as a result of IS interruption for non-compliance or medical decision, especially post-transplant lymphoproliferative disorder (PTLD) [12, 13]. These patients display stable and good graft function for years, respond to immunological challenge [12] and do not harbour more opportunistic infections than healthy volunteers [12, 13]. From a clinical point of view, these patients, who are mainly discovered fortuitously [12, 14, 15], are comparable with renal recipients with stable graft function under standard IS (STA), with only few differences including increase proportion of graft from living donors and lower levels of HLA mismatch [12].

To date, no clinical parameter safely permitted to wean off IS, even in trials based on a drastic selection of non-sensitized recipients with highly stable graft function [16, 17](Dugast E et al., Am J Transplant. 2016 November; 16(11):3255-3261). Thus, it is clear that intentional replication of withdrawal of IS in renal transplantation in new trials requires clinical parameters but also new laboratory tests that recent reports have paved the way for. Recently, an integrative meta-analysis of these different studies further highlighted 20 genes, mainly B-cell related, as the most significantly differentially expressed genes between TOL and STA [18]. Interestingly, B-cells from these recipients harbour a specific phenotype with expression of inhibitory receptors [24], a unique differentiation profile [27] and display suppressive properties [28]. Collectively, these data suggest that B-cells may not only be potential biomarkers but may also actively regulate the immune response to the transplanted kidney, their induction and expansion being likely favoured by induction therapies [26].

Whereas the utility of such signatures is now clearly established and results from the effort of the scientific community in the last decades [29, 30], we now need to demonstrate their safety and reliability for minimization of IS and follow-up of patients in transplantation. First, we need a signature which is the most reliable while applicable easily to the higher number of patients. Second, we need a signature to be stable and not influenced by events occurring during transplanted patients' life, such as malignancy or immunosuppression. Third, while induction of tolerance is a promising therapeutic way, whether these protocols recapitulate what is observed in operationally tolerant patients or if there are different situations of so-called "tolerance" has not been solved yet, thus, a common signature for the two situations remains to be demonstrated.

SUMMARY

The present invention relates to a method for discriminating an operationally tolerant (TOL) subject from a non-operationally tolerant (STA) subject, comprising the following steps:

i) establishing a composite score of tolerance (cSoT) with the expression levels of six genes in a biological sample obtained from said subject and two clinical parameters; wherein said cSoT is established by the following formula:

$$cSoT = \sum_i^n = \beta_i \times Exprs + \beta_{test\ time} \times age_{test\ time} + \beta_{trans\ time} \times age_{trans\ time} + intercept - scaling\ coefficient$$

ii) comparing this cSoT with a predetermined reference value; and iii) concluding that the subject is TOL when the cSoT is higher than the predetermined reference value or concluding that the subject is STA when the cSoT is lower than the predetermined reference value.

In one embodiment, the six genes are ID3, AKR1C3, CD40, CTLA4, TCL1A and MZB1.

In one embodiment, the two clinical parameters are the age of said subject at test time and the age of said subject at transplantation time.

In one embodiment, the predetermined reference value is the cSoT of a TOL subject. In another embodiment, the predetermined reference value is the cSoT of a STA subject.

In one embodiment, the subject is under immunosuppressive treatment.

In one embodiment, the subject is a human.

In one embodiment, the subject is a kidney recipient. In one embodiment, said kidney recipient has further been grafted with the pancreas, and optionally with a piece of duodenum of the kidney donor.

The present invention further relates to a method of treating a transplanted subject with an immunosuppressive therapy comprising the steps of:

i) determining whether the subject is an operationally tolerant (TOL) subject or a non-operationally tolerant (STA) subject using the method for discriminating a TOL from a STA subject according to the present invention; and ii) treating the subject with immunosuppressive therapy when the subject is STA.

The present invention also relates to a method for identifying a transplanted subject under immunosuppressive therapy as a candidate for immunosuppressive therapy weaning or minimization, comprising the steps of:

i) determining whether the subject is an operationally tolerant (TOL) subject or a non-operationally tolerant (STA) subject using the method for discriminating a TOL from a STA subject according to the present invention; and ii) concluding that the subject is eligible to immunosuppressive therapy weaning or minimization when the subject is TOL.

DEFINITIONS

In the present invention, the following terms have the following meanings:

As used herein, the term "AKR1C3" refers to aldo-keto reductase family 1 member C3. The naturally occurring human AKR1C3 gene has a nucleotide sequence as shown in Genbank Accession number NM_001253908.1 and the naturally occurring human AKR1C3 protein has an amino acid sequence as shown in Genbank Accession number NP_001240837.1.

As used herein, the term "biological sample" refers to any sample obtained from a subject, preferably from a transplanted subject, such as a serum sample, a plasma sample, a urine sample, a blood sample, a lymph sample, or a biopsy. In a particular embodiment, the biological samples for the determination of a gene expression level include samples such as a blood sample, a lymph sample, or a biopsy. In a particular embodiment, the biological sample is a blood sample, more particularly, peripheral blood mononuclear cells (PBMC). Typically, these cells can be extracted from whole blood using Ficoll, a hydrophilic polysaccharide that separates layers of blood, with the PBMC forming a cell ring under a layer of plasma. Additionally, PBMC can be extracted from whole blood using a hypotonic lysis which will preferentially lyse red blood cells. Such procedures are known to the expert in the art.

As used herein, the term "CD40" refers to cluster of differentiation 40. CD40 is a costimulatory protein found on antigen presenting cells and is required for their activation. The naturally occurring human CD40 gene has a nucleotide sequence as shown in Genbank Accession number NM_001250.5 and the naturally occurring human CD40 protein has an amino acid sequence as shown in Genbank Accession number NP_001241.1. The murine nucleotide and amino acid sequences have also been described (Genbank Accession numbers NM_011611.2 and NP_035741.2, respectively).

As used herein, the term "CTLA4" refers to cytotoxic T-lymphocyte-associated protein 4, also known as CD152 (cluster of differentiation 152). It is a protein receptor that, functioning as an immune checkpoint, downregulates immune responses. The naturally occurring human CTLA4 gene has a nucleotide sequence as shown in Genbank Accession number NM_001037631.2 and the naturally occurring human CTLA4 protein has an amino acid sequence as shown in Genbank Accession number NP_001032720.1. The murine nucleotide and amino acid sequences have also been described (Genbank Accession numbers NM_001281976.1 and NP_001268905.1, respectively).

As used herein, the term "discriminating" refers to identify, observe a difference or distinguish two groups. Typically, the method according to the invention is suitable to identify or distinguish a subject who is tolerant among subjects treated with an immunosuppressive drug.

As used herein, the term "ID3" refers to inhibitor of DNA binding 3. The naturally occurring human ID3 gene has a nucleotide sequence as shown in Genbank Accession number NM_002167.4 and the naturally occurring human ID3 protein has an amino acid sequence as shown in Genbank Accession number NP_002158.3. The murine nucleotide and amino acid sequences have also been described (Genbank Accession numbers NM_008321.2 and NP_032347.1, respectively).

As used herein, the terms "immunosuppressive therapy" or "immunosuppressive treatment" refer to the administration to a transplanted subject of one or more immunosuppressive drugs. Immunosuppressive drugs that may be employed in transplantation procedures include, but are not limited to, azathioprine, methotrexate, cyclophosphamide, FK-506 (tacrolimus), sirolimus, everolimus, rapamycin, corticosteroids, cyclosporins (such as, e.g., cyclosporin A), mycophenolic acid, leflumacide, ascomycin and hydroxyurea. These drugs may be used in monotherapy or in combination therapies.

As used herein, the term "immunosuppressive therapy weaning or minimization" refers to the progressive reduction, and optionally eventually the suppression, of an immunosuppressive therapy in a transplanted subject being administered with immunosuppressive drugs.

As used herein, the term "MZB1" refers to marginal zone B and B1 cell-specific protein 1. The naturally occurring human MZB1 gene has a nucleotide sequence as shown in Genbank Accession number NM_016459.3 and the naturally occurring human TCL1A protein has an amino acid sequence as shown in Genbank Accession number NP_057543.2. The murine nucleotide and amino acid sequences have also been described (Genbank Accession numbers NM_027222.3 and NP_081498.2, respectively).

As used herein, the term "organ transplantation" refers to the procedure of replacing diseased organs, parts of organs, or tissues by healthy organs or tissues. The transplanted organ or tissue can be obtained either from the subject himself (=autograft), from another human donor (=allograft) or from an animal (=xenograft). Transplanted organs may be artificial or natural, whole (such as kidney, heart and liver) or partial (such as heart valves, skin and bone).

As used herein, the term "predetermined reference value" refers to a threshold value or a cut-off value. Typically, a "threshold value" or "cut-off value" can be determined experimentally, empirically, or theoretically. A threshold value can also be arbitrarily selected based upon the existing experimental and/or clinical conditions, as would be recognized by a person of ordinary skilled in the art. For example, retrospective measurement in properly banked historical subject samples may be used in establishing the predetermined reference value. The threshold value has to be determined in order to obtain the optimal sensitivity and specificity according to the function of the test and the benefit/risk balance (clinical consequences of false positive and false negative). Typically, the optimal sensitivity and specificity (and so the threshold value) can be determined using a Receiver Operating Characteristic (ROC) curve based on experimental data. For example, after determining the expression level of the selected peptide in a group of reference, one can use algorithmic analysis for the statistic treatment of the expression levels determined in samples to be tested, and thus obtain a classification standard having significance for sample classification. The full name of ROC curve is receiver operator characteristic curve, which is also known as receiver operation characteristic curve. It is mainly used for clinical biochemical diagnostic tests. ROC curve is a comprehensive indicator that reflects the continuous variables of true positive rate (sensitivity) and false positive rate (1-specificity). It reveals the relationship between sensitivity and specificity with the image composition method. A series of different cut-off values (thresholds or critical values, boundary values between normal and abnormal results of diagnostic test) are set as continuous variables to calculate a series of sensitivity and specificity values. Then sensitivity is used as the vertical coordinate and specificity is used as the horizontal coordinate to draw a curve. The higher the area under the curve (AUC), the higher the accuracy of diagnosis. On the ROC curve, the point closest to the far upper left of the coordinate diagram is a critical point having both high sensitivity and high specificity values. The AUC value of the ROC curve is between 1.0 and 0.5. When AUC>0.5, the diagnostic result gets better and better as AUC approaches 1. When AUC is between 0.5 and 0.7, the accuracy is low. When AUC is between 0.7 and 0.9, the accuracy is moderate. When AUC is higher than 0.9, the accuracy is high. This algorithmic method is preferably done with a computer. Existing software or systems in the art may be used for the drawing of the ROC curve, such as: MedCalc 9.2.0.1 medical statistical software, SPSS 9.0, ROCPOWER.SAS, DESIGNROC.FOR, MULTIREADER POWER.SAS, CREATE-ROC.SAS, GB STAT VI0.0 (Dynamic Microsystems, Inc. Silver Spring, Md., USA), etc.

As used herein, the term "reagent for the determination of a gene expression level" is meant a reagent which specifically allows for the determination of said gene expression level, i.e., a reagent specifically intended for the specific determination of the expression level of a given gene, such as, e.g., of the ID3, AKR1C3, CD40, CTLA4, TCL1A and/or MZB1 genes. This definition therefore excludes generic reagents useful for the determination of the expression level of any gene, such as taq polymerase or an amplification buffer, although such generic reagents may be necessary, albeit not sufficient, to determine the expression level of a given gene, and may therefore also be included in a kit according to the invention.

As used herein, the term "STA" refers to a "non-operationally tolerant subject", i.e., the subject is under immunosuppression with stable function, but would reject his/her graft if the immunosuppressive treatment was withdrawn. Such subject is considered as non-tolerant to the graft. In a particular embodiment, the subject "STA" is considered as having a high immunologic risk, i.e., said subject has a higher risk of developing rejection (acute or chronic) and/or antibodies against the graft.

As used herein, the term "subject" refers to any mammals, such as a rodent, a feline, a canine, and a primate. Particularly, in the present invention, the subject is a human, also termed "patient". In a particular embodiment, the subject is a transplanted subject, also termed "recipient" or "grafted subject".

As used herein, the term "TCL1A" refers to T-cell leukaemia or lymphoma protein 1. The naturally occurring human TCL1A gene has a nucleotide sequence as shown in Genbank Accession number NM_001098725.1 and the naturally occurring human TCL1A protein has an amino acid sequence as shown in Genbank Accession number NP_001092195.1.

As used herein, the term "TOL" refers to an "operationally tolerant subject", i.e., the subject is under immunosuppression with stable function for which immunosuppression regimen can be safely withdrawn. It means that the subject does not reject his/her graft in the absence of an immunosuppressive treatment with a well-functioning graft. Such subject is considered as tolerant to the graft. In a particular embodiment, the subject "TOL" is considered as having a low immunologic risk, i.e., said subject has a lower risk of developing rejection (acute or chronic) and/or antibodies against the graft.

As used herein, the term "transplanted subject" (also called "recipient" or "grafted subject"), refers to a subject who has received an organ transplantation.

As used herein, the terms "treating" and "treatment" refer to both prophylactic or preventive treatment, as well as curative or disease-modifying treatment, including treatment of subject at risk of contracting the disease or suspected to have contracted the disease, as well as subject who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a subject during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a subject during treatment of an illness, e.g., to keep the subject in remission for long periods of time (months or years). A maintenance regimen may employ continuous therapy (e.g., administering a drug at regular intervals, e.g., weekly, monthly, yearly, etc.) or intermittent therapy (e.g., interrupted treatment, intermittent treatment, treatment at relapse, or treatment upon achievement of a particular predetermined criteria [e.g., pain, disease manifestation, etc.]).

As used herein, the term "two clinical parameters" refers to the age of the subject at the test time and the age of the subject at the transplantation time.

DETAILED DESCRIPTION

Based on the 20-gene signature from their published meta-analysis, Inventors used a sparse methodology to identify and validate the most informative genes that, in association with few demographic parameters, allow to construct a predictive score of tolerance applicable in clinical routine

[31]. The Inventors thus identified and validated a score of 6 genes combined with 2 basic clinical parameters that allow identifying TOL from STA with excellent accuracy. They showed that this signature of tolerance is not compromised by the malignancy (PTLD) status of the patients, centre origin, neither by IS treatment. Operationally tolerant recipients and patients who benefit from a protocol of tolerance induction do not share a common "tolerance signature". Finally, they showed that this score was influenced by de novo anti-HLA antibody, including DSA and tolerance loss, which reinforced its potential to follow renal transplanted patients.

Accordingly, in a first aspect, the invention relates to a method for discriminating an operationally tolerant (TOL) subject from a non-operationally tolerant (STA) subject, comprising the following steps:

i) establishing a composite score of tolerance (cSoT) with the expression level of at least two, at least three, at least four, at least five, at least six or more genes in a biological sample obtained from said subject and at least one, at least two or more clinical parameters; wherein, said score is established by the following formula:

$$cSoT = \sum_{i}^{n} = \beta_i \times Exprs + \beta_{test\ time} \times age_{test\ time} + \beta_{trans\ time} \times age_{trans\ time} + \text{intercept} - \text{scaling coefficient}$$

ii) comparing said cSoT with a predetermined reference value; and
iii) concluding that the subject is TOL when said cSoT is higher than the predetermined reference value or concluding that the subject is STA when said cSoT is lower than the predetermined reference value.

In one embodiment, the genes are selected from the group consisting of ID3, AKR1C3, CD40, CTLA4, TCL1A, MZB1, CD22, BLK, MS4A1, CD79B, BLNK, FCRL2, IRF4, HINT1, RFC4, ANXA2R, FCER2, AKIRIN2, EPS15 and PLBD1. Preferably, the genes are selected from the group consisting of ID3, AKR1C3, CD40, CTLA4, TCL1A and MZB1.

In one embodiment, the clinical parameters are selected from the group consisting of the age of said subject at test time, the age of the subject at transplantation time, the donor age, the recipient gender, the donor gender, the donor type, the graft order, the number of HLA mismatches, the induction treatment, the recipient's creatinemia, the recipient's proteinuria, the presence in the recipient of anti-HLA Ab at test time and the presence in the recipient of DSA at test time. Preferably, the clinical parameters are selected from the group consisting of the age of said subject at test time and the age of the subject at transplantation time.

In one embodiment, the method for discriminating a subject TOL from STA comprises the following steps:

i) establishing a composite score of tolerance (cSoT) with the expression level of at least two, at least three, at least four, at least five, at least six or more genes selected from the group consisting of ID3, AKR1C3, CD40, CTLA4, TCL1A and MZB1 in a biological sample obtained from said subject and at least one, at least two or more clinical parameters selected from the group consisting of the age of said subject at test time and the age of the subject at transplantation time; wherein, said score is established by the following formula:

$$cSoT = \sum_{i}^{n} = \beta_i \times Exprs + \beta_{test\ time} \times age_{test\ time} + \beta_{trans\ time} \times age_{trans\ time} + \text{intercept} - \text{scaling coefficient}$$

ii) comparing said cSoT with a predetermined reference value; and
iii) concluding that the subject is TOL when said cSoT is higher than the predetermined reference value or concluding that the subject is STA when said cSoT is lower than the predetermined reference value.

In one embodiment, the method for discriminating a subject TOL from STA comprises the following steps:

i) establishing a composite score of tolerance (cSoT) with the expression level of six genes ID3, AKR1C3, CD40, CTLA4, TCL1A, MZB1 in a biological sample obtained from said subject and two clinical parameters selected from the age of said subject at test time and the age of the subject at transplantation time; wherein, said score is established by the following formula:

$$cSoT = \sum_{i}^{n} = \beta_i \times Exprs + \beta_{test\ time} \times age_{test\ time} + \beta_{trans\ time} \times age_{trans\ time} + \text{intercept} - \text{scaling coefficient}$$

ii) comparing said cSoT with a predetermined reference value; and
iii) concluding that the subject is TOL when said cSoT is higher than the predetermined reference value or concluding that the subject is STA when said cSoT is lower than the predetermined reference value.

In one embodiment, a TOL subject maintains stable graft function off immunosuppressive drugs. In one embodiment, a STA subject does not maintain stable graft function off immunosuppressive drugs.

In one embodiment, the subject is a mammal. In a particular embodiment, the subject is a human.

In one embodiment, the subject is a transplanted subject. In a particular embodiment, the subject is a renal-transplanted subject. In particular, said renal-transplanted subject may further have been grafted with the pancreas, and optionally a piece of duodenum, of the kidney donor.

In one embodiment, the subject is treated with immunosuppressive drugs or other drugs that are currently known in the art or that will be identified in the future. In a particular embodiment, the subject is under immunosuppressive treatment, i.e., the subject is administered with one or more immunosuppressive drugs.

Immunosuppressive drugs that may be employed in transplantation procedures include, but are not limited to, azathioprine, methotrexate, cyclophosphamide, FK-506 (tacrolimus), sirolimus, everolimus, rapamycin, corticosteroids, cyclosporins (such as, e.g., cyclosporin A), mycophenolic acid, leflumacide, ascomycin and hydroxyurea.

In one embodiment, immunosuppressive drugs are used in monotherapy. In another embodiment, immunosuppressive drugs are used in combination therapies.

In the case of renal transplantation, the following immunosuppressive protocols are usually used. Subjects with primary renal transplantation generally receive an induction treatment consisting of 2 injections of basiliximab (Simulect®, a chimeric murine/human monoclonal anti-IL2-Rα antibody commercialized by Novartis), in association with tacrolimus (Prograf™, Fujisawa Pharmaceutical, 0.1 mg/kg/day), mycophenolate mofetil (Cellcept™, Syntex Laboratories, Inc., 2 g/day) and corticoids (1 mg/kg/day), the corticoid treatment being progressively decreased by 10 mg every 5 days until end of treatment, 3 months post-transplantation. Subjects with secondary or tertiary renal transplantation, or subjects considered at immunological risk (percentage of anti-T panel reactive antibodies (PRA) previously peaking above 25% or cold ischemia for more than 36 hours), generally receive a short course of anti-thymocyte globulin (ATG) (for, e.g., 7 days), in addition from day 0 with mycophenolate mofetil (Cellcept™, Syntex Laboratories, Inc, 2 g/day), and corticosteroids (1 mg/kg/day), then the steroids are progressively tapered by 10 mg every 5 days until end of treatment and finally stopped around 3 months post-transplantation. Tacrolimus (Prograf™, Fujisawa Pharmaceutical) is introduced in a delayed manner (at day 6) at a dose of 0.1 mg/kg/day.

As used herein, the term "composite score of tolerance (cSoT)", also referred to as "score", refers to a value obtained from the following formula:

$$cSoT = \sum_{i}^{n} = \beta_i \times Exprs + \beta_{test\ time} \times age_{test\ time} + \beta_{trans\ time} \times age_{trans\ time} + intercept - scaling\ coefficient$$

This formula was obtained by using the Bolasso algorithm, a lasso (Least Absolute Selection and Shrinkage Operator) analysis performed by bootstrap resampling (10,000 times) followed by multiple testing (false discovery rate<0.05), which allows to identify the eight parameters (six genes and two clinical parameters) of the present invention.

Within the meaning of the invention, the term "β" refers to a coefficient for each gene according to the invention.

"$\beta_i$" represent the regression β coefficient for each gene. Typically, the regression β coefficients are determined by the skilled man in the art for each gene using the Bolasso method as described in Erickson, K. F., et al., 2016. Typically, a blood sample can be obtained from a subject transplanted and treated under IS; and the expression of 6 genes can be determined by conventional methods.

Two clinical parameters (the subject's age at the test time [$age_{test\ time}$] and the subject's age at the transplantation time [$age_{trans\ time}$]) are taken into consideration. The score is then compared with a cut-off value that distinguishes TOL or STA. The cut-off value can be determined by analysing the expression of the same genes via the same analysis method in non-transplanted subjects and in transplanted subjects. For example, it can be the middle point between the score of non-transplanted subjects and that of transplanted subjects.

As used herein, the term "$\beta_{test\ time}$" refers to the β coefficient of the age of the subject at the test time.

As used herein, the term "$\beta_{trans\ time}$" refers to the β coefficient of the age of the subject at the transplantation time.

As used herein, the term "intercept" refers to a fixed value used to correct the equation (refers to the interception of the regression curve to the Y axis).

As used herein, the term "scaling coefficient" refers to a value used to centre the score in order to associate positive and negative scores with TOL and STA diagnosis, respectively.

As used herein, the term "Exprs" refers to the expression level of each gene. The "gene expression profile" corresponds to a group of at least 2, 3, 4, 5, 6 or more values corresponding to the gene expression level of each of at least 2, 3, 4, 5, 6 or more genes selected from the group consisting of ID3, AKR1C3, CD40, CTLA4, TCL1A, MZB1, CD22, BLK, MS4A1, CD79B, BLNK, FCRL2, IRF4, HINT1, RFC4, ANXA2R, FCER2, AKIRIN2, EPS15 and PLBD1, optionally with further other values corresponding to the clinical parameters. Preferably, the gene expression profile corresponds to a group of 6 values corresponding to the gene expression level of each of the ID3, AKR1C3, CD40, CTLA4, TCL1A and MZB1 gene, optionally with further other values corresponding to the clinical parameters. Typically, the expression level of the genes, preferably of the 6 genes, may be determined by any technology known by a person skilled in the art. In particular, each gene expression level may be measured at the genomic and/or nucleic and/or protein level. In a particular embodiment, the expression level of gene is determined by measuring the amount of nucleic acid transcripts of each gene. In another embodiment, the gene expression level is determined by measuring the amount of each gene corresponding protein. The amount of nucleic acid transcripts can be measured by any technology known by a man skilled in the art. In particular, the measure may be carried out directly on an extracted messenger RNA (mRNA) sample, or on retrotranscribed complementary DNA (cDNA) prepared from extracted mRNA by technologies well-known in the art. From the mRNA or cDNA sample, the amount of nucleic acid transcripts may be measured using any technology known by a man skilled in the art, including nucleic microarrays, quantitative PCR, microfluidic cards, and hybridization with a labelled probe. In a particular embodiment, the gene expression level is determined using quantitative PCR. Quantitative, or real-time, PCR is a well-known and easily available technology for those skilled in the art and does not need a precise description. Methods for determining the quantity of mRNA are well known in the art. For example, the nucleic acid contained in the biological sample is first extracted according to standard methods, for example using lytic enzymes or chemical solutions or extracted by nucleic-acid-binding resins following the manufacturer's instructions. The extracted mRNA is then detected by hybridization (e. g., Northern blot analysis) and/or amplification (e.g., RT-PCR). Preferably quantitative or semi-quantitative RT-PCR is preferred. Real-time quantitative or semi-quantitative RT-PCR is particularly advantageous.

Other methods of amplification include ligase chain reaction (LCR), transcription-mediated amplification (TMA), strand displacement amplification (SDA) and nucleic acid sequence based amplification (NASBA).

Nucleic acids having at least 10 nucleotides and exhibiting sequence complementarity or homology to the mRNA of interest herein find utility as hybridization probes or amplification primers. It is understood that such nucleic acids need not be identical, but are typically at least about 80% identical to the homologous region of comparable size, more preferably 85% identical, even more preferably 90% identical, even more preferably 95% or more identical to the homologous region of comparable size. In certain embodiments, it will be advantageous to use nucleic acids in combination with appropriate means, such as a detectable label, for detecting hybridization. A wide variety of appropriate indicators are known in the art including, fluorescent, radioactive, enzymatic or other ligands (e.g., avidin/biotin).

Probes typically comprise single-stranded nucleic acids of between 10 to 1000 nucleotides in length, for instance of between 10 and 800, more preferably of between 15 and 700, typically of between 20 and 500. Primers typically are shorter single-stranded nucleic acids, of between 10 to 25 nucleotides in length, designed to perfectly or almost perfectly match a nucleic acid of interest, to be amplified. The probes and primers are "specific" to the nucleic acids they hybridize to, i.e., they preferably hybridize under high stringency hybridization conditions (corresponding to the highest melting temperature Tm, e.g., 50% formamide, 5× or 6×SCC buffer. 1×SCC buffer comprises 0.15 M NaCl and 0.015 M Na-citrate, adjusted to pH 7.0 with HCl).

The nucleic acid primers or probes used in the above amplification and detection method may be assembled as a kit. Such a kit includes consensus primers and molecular probes. A kit also includes the components necessary to determine if amplification has occurred. The kit may also include, for example, PCR buffers and enzymes; positive control sequences, reaction control primers; and instructions for amplifying and detecting the specific sequences.

In a particular embodiment, the method of the invention comprises the steps of providing total RNAs extracted from a biological sample and subjecting the RNAs to amplification and hybridization to specific probes, more particularly by means of a quantitative or semi-quantitative RT-PCR.

In another embodiment, the gene expression level is determined by DNA chip analysis. Such DNA chip or nucleic acid microarray consists of different nucleic acid probes that are chemically attached to a substrate, which can be a microchip, a glass slide or a microsphere-sized bead. A microchip may be constituted of polymers, plastics, resins, polysaccharides, silica or silica-based materials, carbon, metals, inorganic glasses, or nitrocellulose. Probes comprise nucleic acids such as cDNAs or oligonucleotides that may be about 10 to about 60 base pairs. To determine the gene expression level, a biological sample from a test subject, optionally first subjected to a reverse transcription, is labelled and contacted with the microarray in hybridization conditions, leading to the formation of complexes between target nucleic acids that are complementary to probe sequences attached to the microarray surface. The labelled hybridized complexes are then detected and can be quantified or semi-quantified. Labelling may be achieved by various methods, e.g., by using radioactive or fluorescent labelling. Many variants of the microarray hybridization technology are available to the man skilled in the art (see e.g. the review by Hoheisel, Nature Reviews, Genetics, 2006, 7:200-210).

The present invention also relates to a method of treating a transplanted subject with an immunosuppressive therapy comprising the steps of:
i) determining whether the subject is an operationally tolerant (TOL) subject or a non-operationally tolerant (STA) subject according to the invention; and
ii) treating the subject with one or more immunosuppressive drugs when the subject is STA.

The present invention also relates to a method for identifying a transplanted subject under immunosuppressive therapy as a candidate for immunosuppressive therapy weaning or minimization, comprising the steps of:

i) determining whether the subject is an operationally tolerant (TOL) subject or a non-operationally tolerant (STA) subject according to the invention; and
ii) concluding that the subject is eligible to immunosuppressive therapy weaning or minimization when the subject is TOL.

In another aspect, the present invention also relates to a kit for discriminating an operationally tolerant (TOL) subject from a non-operationally tolerant (STA) subject, comprising at least one reagent for the determination of a gene expression profile corresponding to a group of at least 2, 3, 4, 5, 6 or more values corresponding to the gene expression level of each of at least 2, 3, 4, 5, 6 or more genes selected from the group consisting of ID3, AKR1C3, CD40, CTLA4, TCL1A, MZB1, CD22, BLK, MS4A1, CD79B, BLNK, FCRL2, IRF4, HINT1, RFC4, ANXA2R, FCER2, AKIRIN2, EPS15 and PLBD1, optionally with further other values corresponding to the clinical parameters. Preferably, the kit according to the present invention comprises at least one reagent for the determination of a gene expression profile corresponding to a group of 6 values corresponding to the expression level of each of the 6 following genes: ID3, AKR1C3, CD40, CTLA4, TCL1A and MZB1.

In one embodiment, the kit according to the present invention may further comprise at least one reagent for the determination of a gene expression level of at least one reference gene. Examples of reference genes include, but are not limited to, ACTB, B2M, GAPDH and HPRT1. In one embodiment, determination of a gene expression level of at least one reference gene is used to normalize and/or calculate the relative expression of each genes according to the present invention.

In some embodiments, the kit according to the invention may further comprise instructions for discriminating a subject TOL from STA. The instructions for the discrimination of a subject TOL from STA may include at least one reference gene expression profile. In a particular embodiment, at least one reference gene expression profile is a graft-tolerant expression profile, i.e., a group of 6 values corresponding to the expression level of each of the 6 following genes: ID3, AKR1C3, CD40, CTLA4, TCL1A and MZB1, in an operationally tolerant (TOL) subject. Alternatively, at least one reference gene expression profile may be a graft-non-tolerant expression profile, i.e., a group of 6 values corresponding to the expression level of each of the 6 following genes: ID3, AKR1C3, CD40, CTLA4, TCL1A and MZB1, in a non-operationally tolerant (STA) subject.

The invention will be further illustrated by the following figures and examples. However, these examples and figures should not be interpreted in any way as limiting the scope of the present invention.

BRIEF DESCRIPTION OF THE DRAWINGS

(FIG. 1B) Receiver operating characteristic (ROC) curves of cSoT [cSoT], combination of the 6 genes (ID3, AKR1C3, CD40, CTLA4, TCL1A and MZB1) [6 genes], age of the patient at test time [Age at collection], age of the patient at transplantation time [Age at Tx] and creatinemia [creatinemia].
(FIG. 1C) cSoT values for 231 patients (42 TOL [grey] and 189 STA [black]). The dashed line represents the centred best threshold of the ROC curve (Youden index). The grey zone (on both side of the dashed line) represents the inconclusive zone defined by values with specificity and specificity below 90%.

Figure 2A:
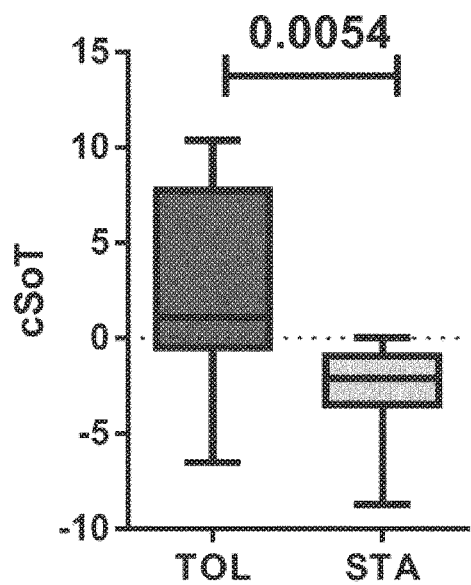
Figure 2B:
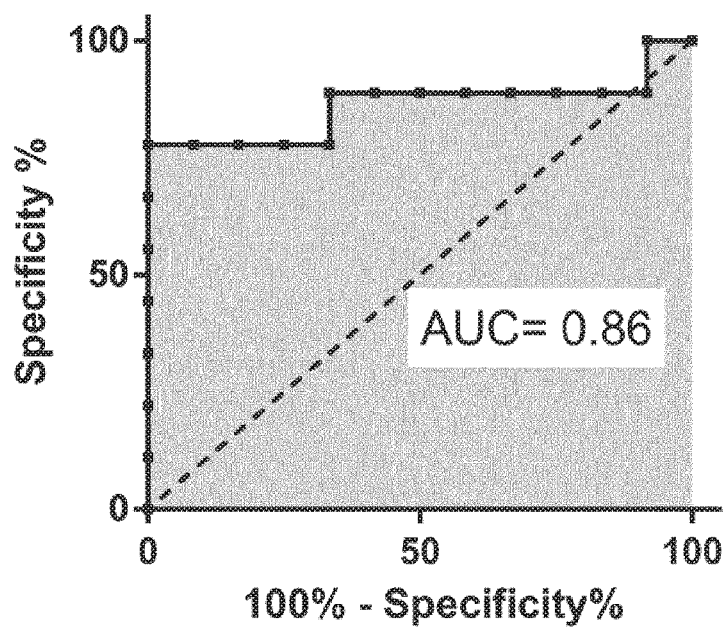

FIGS. 2A and 2B: cSOT validated using qPCR (FIG. 2A) Using qPCR, cSoT was still differential between TOL and STA (n=9 and 12; mean=2.89±5.41 and −2.58±2.37, respectively) and (FIG. 2B) displayed an AUC of 0.86 $IC_{95\%}$ [0.66-1]).

EXAMPLES

Material & Methods

Meta-Analysis Dataset

Gene expression dataset was obtained from Gene Expression Ominbus (GEO) database (accession number GSE28456) previously described [18]. This dataset was the result of a meta-analysis from 5 independent studies gathering 596 samples [14, 15, 21, 50, 51].

Briefly, datasets were renormalized using a Lowess procedure, log-transformed, and median-centred according to the STA group as previously described and composed of 1,846 merged genes [18]. In addition to Nantes' collection and thanks to the European IoT and the American ITN networks, we were able to identify 344 unique non-redundant patients among the different studies: 46 individual operationally tolerant patients (TOL) out of 96 TOL samples and 266 patients with stable graft function (STA) out of 311 STA samples. Demographic description of available clinical parameters from TOL and STA patients are given in Table 1 and Table 2. Mean expression for each of the 20 genes was calculated in case of technical replicates (identical blood sample time) and earliest time point was selected in case of time replicates.

TABLE 1 demographic parameters of TOL (n = 46) and STA (n = 199)

|  | TOL | | | STA | | | T.test |
| --- | --- | --- | --- | --- | --- | --- | --- |
|  | Mean | sd | n | Mean | sd | n | p.value |
| Age of the patient at test time | 49.89 | 13.00 | 45 | 52.94 | 13.64 | 190 | 0.175 |
| Time post-transplantation | 18.30 | 9.302 | 42 | 9.32 | 3.948 | 198 | <0.0001 |
| Time post-treatment | 7.914 | 9.018 | 45 | NA | NA | NA | NA |
| Age of the patient at transplantation time | 31.66 | 13.25 | 42 | 43.71 | 14.00 | 190 | <0.0001 |
| Creatinemia | 106 | 30.62 | 44 | 118.8 | 31.06 | 190 | 0.0144 |
| Proteinuria | 0.213 | 0.247 | 12 | 0.207 | 0.207 | 178 | 0.915 |
| Donor age | 36.84 | 19.19 | 25 | 35.54 | 14.36 | 167 | 0.684 |

TABLE 2 demographic parameters of TOL (n = 46) and STA (n = 199).

|  | TOL | | STA | | Fisher |
| --- | --- | --- | --- | --- | --- |
|  | n | | n | | p.value |
| Recipient gender (M/F) | 29/16 | 45 | 116/75 | 191 | 0.734 |
| Donor gender (M/F) | 20/12 | 32 | 125/45 | 167 | 0.192 |
| Donor type (NLD/LD) | 15/7 | 22 | 191/0 | 191 | <0.0001 |
| Graft order (1/2) | 16/6 | 32 | 191/0 | 191 | <0.0001 |
| HLA MM (0, 1, 2, 3, 4, 5, 6) | 14, 3, 5, 7, 5, 1, 1 | 36 | 5, 7, 31, 41, 45, 30, 8 | 167 | <0.0001 |
| Induction treatment (Y/N) | 10/6 | 16 | 125/42 | 167 | 0.371 |
| Presence of anti-HLA Ab at test time (Y/N) | 7/8 | 15 | 24/137 | 161 | 0.0013 |
| Presence of DSA at test time (Y/N) | 9/4 | 13 | 141/14 | 168 | 0.036 |

M/F: male/female
NLD/LD: non-living donor/living donor
1/2: primary/secondary
HLA MM: human leukocyte antigen mismatch (0 to 6 mismatches)
Y/N: Yes/No
DSA: donor-specific antibodies Additional Microarray Datasets Three publicly available microarray datasets were collected from GEO: GSE14630 [34], GSE22224 [35] and GSE45593[8] and normalized with the robust multi-array average method (RMA) using the affy package [52] in the R software. Normalized collected expression values from dataset GSE45218 [33] were used for in silico cross-validation. For all datasets, gene expressions of the 6 genes of interest were centred/scaled before applying coefficients of the cSoT.

Validation Cohort

Additional 21 kidney recipients from Nantes' Hospital were enrolled to perform qPCR validation, including 9 TOL and 12 STA. Local Ethic Committee approved all aspects of this study and all patients gave their written informed consent.

qPCR Validation

Venous blood samples were collected in EDTA vacutainers and processed for analysis within 4 hours. Peripheral Blood Mononuclear Cells (PBMC) were separated on a Ficoll layer (Eurobio, Les Ulis, France) and frozen in TRIzol® reagent (Thermo Fisher Scientific, Waltham, Mass. USA) at −80° C. RNA was extracted from peripheral blood using the TRIzol method (Thermo Fisher Scientific). RNA quality and quantity were determined using an Agilent 2100 BioAnalyzer (Palo Alto, Calif., USA) and a Nanodrop (Labtech, Palaiseau, France), respectively. RNA was reverse-transcribed using poly-dT oligonucleotides and Maloney leukaemia virus reverse transcription (Thermo Fisher Scientific). Real-time quantitative PCR was performed on a StepOnePlus instrument (Thermo Fisher Scientific) using commercially available primer and probe sets (Taqman) for the 6 tested genes and 4 reference genes: AKR1C3: Hs00366267_m1, CD40: Hs00374176_m1, CTLA4: Hs00175480_m1, ID3: Hs00171409_m1, MZB1

(or MGC29506): Hs00414907_m1, TCL1A: Hs00951350_m1; and 4 reference genes: ACTB: Hs99999903_m1, B2M: Hs00984230_m1, GAPDH: Hs99999905_m1, HPRT1: Hs99999909_m1 (Thermo Fisher Scientific). The geometric mean of the 4 reference genes was used to normalize for RNA amounts and to calculate the relative expression of each genes according to the $2^{-\Delta\Delta Cq}$ method [53].

cSoT Construction

Parameters associated with TOL compared to STA in logistic univariate analysis (using glm package in R) were used for cSoT construction. To identify the most discriminative combination between the 24 parameters associated with tolerance in univariate analysis (20 genes and 4 demographic parameters), we used the Bolasso method [5] which performs bootstrap resampling (10,000 fold) combined with a lasso (least absolute shrinkage and selection operator) regression analysis followed by multiple testing to select the significant variables associated with the model (False Discovery Rate (FDR)<0.05) using the mht package (version 3.2.2) in R [2]. Coefficients obtained from mht were used to calculate the score from other datasets after scaling, as performed by the mht package. For qPCR data, scaled-dCq were used.

Statistical Analysis

Statistical analyses were performed using R software version 3.2.2 or GraphPrism v.4 software. Parametric student T test, ANOVA test or $Khi^2$ test were used for group comparisons. Differences were defined as statistically significant when p<0.05.

Results

Selection of Clinical Parameters Associated with Operational Tolerance Status

From the meta-dataset we previously described [18], in addition to Nantes' collection and thanks to the European Indice of Tolerance (IoT) and the American Immune Tolerance Networks (ITN), we were able to identify 312 non-redundant patients among the different studies: 46 individual operationally tolerant patients (TOL) out of 96 TOL samples and 266 patients with stable graft function (STA) out of 311 STA samples. Demographic description of available clinical parameters from TOL and STA patients are given in Table 1 and Table 2. In order to construct a predictor score, we selected among demographic clinical parameters of the patients only intrinsic and non-variant patient-related ones and known for at least half of the TOL (Table 1 and Table 2). 4 parameters were associated with tolerance status using univariate logistic regression (p<0.20) and were selected for the composite score: age of the patient at transplantation time (p<0.0001), age of the patient at test time (p=0.176) (Table 1), number of HLA mismatches (p<0.0001) and donor gender (p=0.154) (Table 2).

Composite Score of Operational Tolerance (cSoT) Combining Genes and Clinical Parameters Mean expression for each of the 20 genes was calculated in case of technical replicates (identical blood sample times) and earliest time point was selected in case of time replicates. Expressions of the 20 genes that were previously reported as differential between TOL and STA [1] were confirmed in univariate analysis in this large cohort of 312 patients (46 TOL and 266 STA; p<0.0001).

To identify the most discriminative combination between the 20 original genes and the 4 clinical parameters selected above to include in the cSoT, we used the Bolasso method [5] which perform bootstrap resampling (10,000 fold) combined with a lasso (least absolute shrinkage and selection operator) regression analysis followed by multiple testing to select the significant variables associated with the model (False Discovery Rate [FDR]<0.05) [2].

Figure 1A:
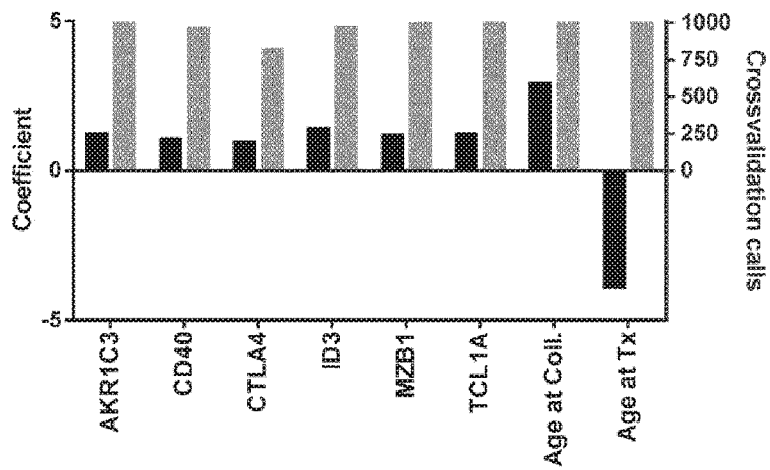
FIGS. 1A-1C: Composite score of tolerance (cSoT)
(FIG. 1A) cSoT model: left axis displays coefficients of selected genes and clinical parameters (False Discovery Rate [fdr]<0.05) (black bars) and right axis represents the number of times, i.e., the occurrence, of selected genes and clinical parameters among the 100 times 10-fold cross-validations (grey bars).
Figure 1B:
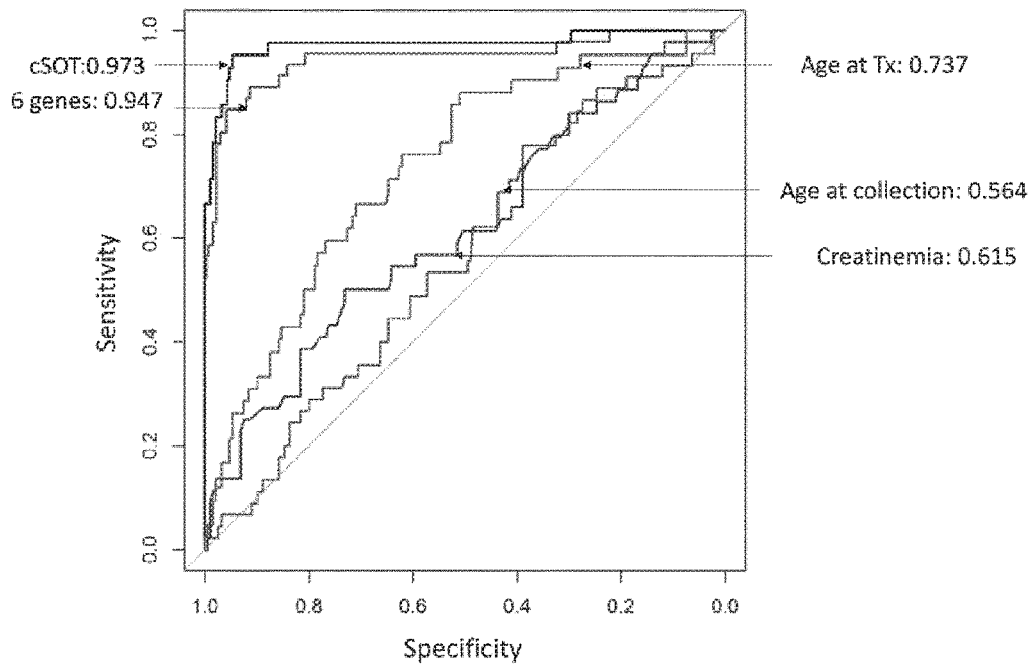
Figure 1C:
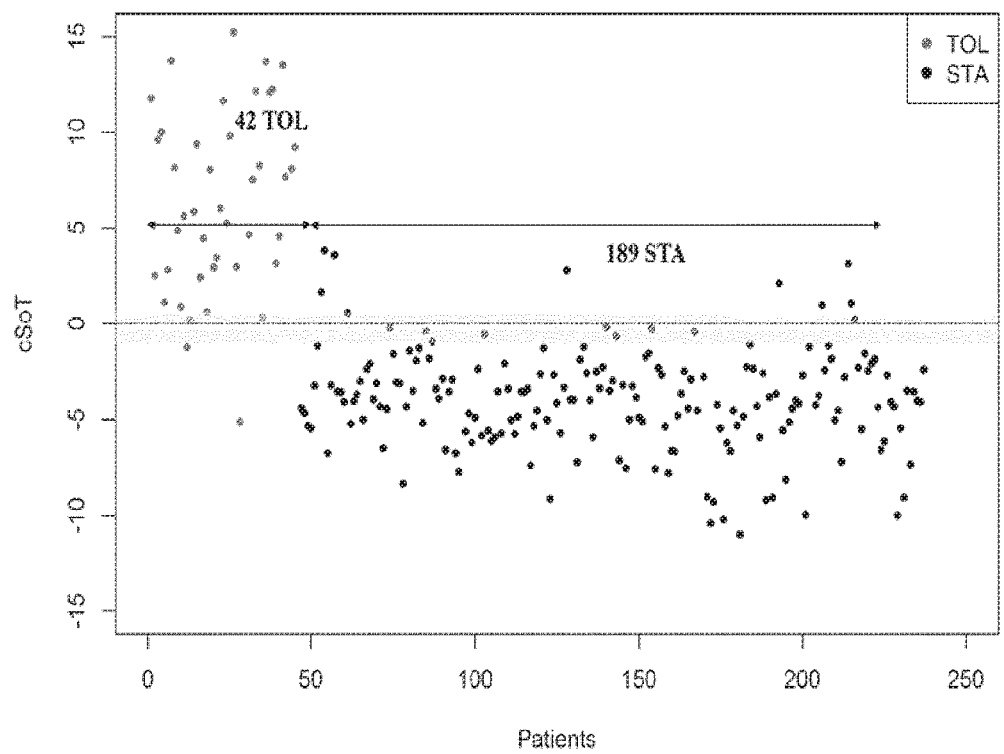

We identified a combination of 6 genes and 2 clinical parameters—AKR1C3, CD40, CTLA4, ID3, MZB1, TCL1A, age of the patient at test time and age of the patient at transplantation time (FIGS. 1A and 1B)—that enabled to establish a cSoT discriminating TOL and STA (mean cSoT=6.43±4.73 (SD) for 42 TOL and −4.04±2.81 for 189 STA; p<0.0001) with an AUC of 0.973 ($IC_{95\%}$ [0.939-1.00]), with negative and positive predictive values of 0.989 and 0.800 respectively (FIGS. 1B and 1C).

The computed cSoT score has been centred using the best threshold of the ROC curve (Youden index) to associate positive and negative scores with TOL and STA diagnosis respectively, and an inconclusive zone (also called "grey zone") has been defined by values with specificity and specificity below 90% (predictive tolerance of 10%) for ease of interpretation (FIGS. 1A-1C) [32]. The consistency of selection of these 8 parameters was validated through a 10-fold cross-validation (randomly one tenth of TOL and STA) repeated 100 times. We found that the 8 selected parameters were present in at least 80% out of the 1,000 models (FIG. 1A).

Finally, the robustness of the cSoT score was further validated through 100 times 10-fold cross-validation with a mean AUC for test sets of 0.967 $IC_{95\%}$ [0.966-0.968]. As attempted, the cSoT score discriminated TOL from STA better than the 2 demographic parameters separately (FIG. 1C): age at transplantation time (AUC=0.737 $IC_{95\%}$ [0.655-0.819]) and age at test time (AUC=0.564, $IC_{95\%}$ [0.474-0.655]; p<0.0001 for both comparisons), better than the combination of the 6 genes only (AUC=0.947 $IC_{95\%}$ [0.902-0.992]; p=0.38) and better then the function of the patients (creatinemia alone (AUC=0.615, $IC_{95\%}$ [0.519-0.711]; p<0.0001).

Finally, for cross-validation, we took advantage of a recent microarray dataset performed on 16 TOL and 9 patients with chronic allograft nephropathy (CAN) [33]. Since individual clinical information were not provided, we could calculate only the combination of the expression 6 genes. Despites our gene combination was not designed to discriminate TOL from CAN but TOL from STA, we could observe significantly different score values (p=0.0061) and a good discrimination between the 2 populations (AUC=0.825 $IC_{95\%}$ [0.636-0.1.014]).

Center Origin, Immunosuppressive Regimen, PTLD, Does Not Influenced the cSoT

Despite TOL samples were coming from 3 different origin (Nantes, IoT and ITN), cSoT was not associated with patient origin (p=0.13). One of the main reasons for IS cessation in patients with stable graft function is the appearance of severe side effects such as PTLD. However, cSoT was not influenced by PTLD experience (PTLD, n=4, p=0.19).

Since the two groups of patients who were used to create the cSoT differed by their immunosuppressive regimen status—STA are under IS whereas TOL received no more IS—we assessed whether IS could impact cSoT values. Regarding the TOL patients, we observed that previous IS regimen before IS withdrawal, including cyclosporine A (CsA), azathioprine, mycophenolic acid (MPA) and use of an induction therapy was not influencing cSoT values (p=0.74, p=0.61, p=0.81 and p=0.51, respectively; 29 TOL). We then analyzed the effect of current IS regimen on the cSoT in the STA population (n=189). Similarly, cSoT was not influenced neither by induction therapy (p=0.97), nor by CsA or Tacrolimus (p=0.64), corticosteroids (p=0.42) and antimetabolite agents (p=0.92). We then further tested the effect of IS regimen on the 6 genes from the cSoT separately or in combination in two independent cohorts of renal transplant recipients with stable graft function with available microarray datasets [34, 35]:

1) a first cohort of patients under CsA (n=14) or rapamycin (Rapa, n=23) monotherapy [7]; and
2) a second cohort of patients after conversion from azathioprine to MPA (n=5 paired before and 3 months after MPA conversion) [6].

In both cohorts, neither the combination of the 6 genes nor the 6 genes independently (data not shown) were modified according to IS regimen (p=0.99 and 0.77, respectively).

Altogether, these data showed that neither the cSoT, nor the genes independently are influenced by previous or maintenance IS treatment.

cSoT is Predictive of Graft Dysfunction and De Novo Antibody Appearance

One of the main question is the stability and the outcome of the cSoT in time. We previously reported that some cases of loss of graft function may be observed in this cohort of TOL [36], with increase of creatinemia (>150 µmol/L) or proteinuria (>1 g/24 h). Among the 15 TOL form Nantes' cohort, for which most clinical information were available, 9 decline their function in time (17.09±3.46 years post-transplantation). In addition, among these 15 TOL, 8 develop de novo anti-HLA antibodies (14.67±1.13 years post-transplantation) and among them, 4 patients develop donor-specific antibodies (DSA; 13.41±0.21 years post-transplantation). Moreover, the presence of de novo anti-HLA antibodies was associated with tolerance loss (p=0.034).

We found that, at the test time, when patients exhibited a good graft function (creatinemia<150 µmol/L and proteinuria<1 g/24 h), cSoT was significantly lower in patients who decline their function (test time 2.29±2.7 years before function decrease) (p=0.047, cSoT=3.79±3.66 and 8.52±4.67) and who develop anti-HLA antibodies and DSA (p=0.016 and p=0.013, respectively) (test time 1.13±1.78 and 0.21±1.10 years before antibody detection).

cSoT is Specific of Operational Tolerance State

To assess the specificity of the cSoT according to operational or protocol-induced tolerance profiles, we tested the cSoT in a trial of tolerance induction, in which renal recipients of HLA-identical from living donors siblings were followed up for 4 years after transplantation [9][8]. The protocol consists in a lymphodepletive alemtuzumab treatment with tacrolimus and MPA with early sirolimus conversion and infusions of donor hematopoietic $CD34^+$ stem cells. Immunosuppression was withdrawn 2 years after transplantation. These patients had a normal biopsy (i.e., no sign of subclinical rejection) and a good renal function at least 1 year after complete IS cessation.

Among the 15 patients, blood transcriptome was followed up to 4 years for 9 of them, 5 who became tolerant and 4 who did not. Either cSoT or the 6 genes only failed to classify the 5 tolerant patients as TOL, before and after arrest of IS, whatever the time post-transplantation. This result thus supports the fact that tolerance from this induction protocol did not share the operational and spontaneous tolerance-related signature, probably because of different mechanisms involved in the two situations, and that this signature is specific of operational tolerance state only.

A qPCR cSoT Applicable in Clinic

Since the cSoT score is based on gene microarray measures, we validated it and confirmed its usefulness using quantitative PCR in order to endorse its possible use in routine. The qPCR was performed into 5 independent TOL samples, not included in the meta-dataset, and 4 TOL from the meta-dataset at different times.

We showed that the cSoT score was discriminating TOL and STA (p=0.0054, n=9 and 12, mean=2.89±5.41 and −2.58±2.37, respectively) with an AUC of 0.861 $IC_{95\%}$ [0.66-1]) (FIGS. 2A and 2B). Furthermore, bootstrap procedure (1,000 times) confirmed the robustness of this validation with a mean AUC of 0.852 ($IC_{95\%}$ [0.845-0.859]).

REFERENCES

Throughout this application, various references describe the state of the art to which this invention pertains. The disclosures of these references are hereby incorporated by reference into the present disclosure.

1. Dantal, J., et al., Effect of long-term immunosuppression in kidney-graft recipients on cancer incidence: randomised comparison of two cyclosporin regimens. Lancet, 1998. 351(9103): p. 623-8.
2. Miller, L. W., Cardiovascular toxicities of immunosuppressive agents. Am J Transplant, 2002. 2(9): p. 807-18.
3. Ojo, A. O., et al., Chronic renal failure after transplantation of a nonrenal organ. N Engl J Med, 2003. 349(10): p. 931-40.
4. Sawinski, D., et al., Calcineurin Inhibitor Minimization, Conversion, Withdrawal, and Avoidance Strategies in Renal Transplantation: A Systematic Review and Meta-Analysis. Am J Transplant, 2016.
5. Erickson, K. F., et al., A Cost Analysis of Tolerance Induction for Two-Haplotype Match Kidney Transplant Recipients. Am J Transplant, 2016. 16(1): p. 371-3.
6. Kawai, T., et al., Long-term results in recipients of combined HLA-mismatched kidney and bone marrow transplantation without maintenance immunosuppression. Am J Transplant, 2014. 14(7): p. 1599-611.
7. Ciancio, G., et al., A randomized pilot study of donor stem cell infusion in living-related kidney transplant recipients receiving alemtuzumab. Transplantation, 2013. 96(9): p. 800-6.
8. Leventhal, J. R., et al., Nonchimeric HLA-Identical Renal Transplant Tolerance: Regulatory Immunophenotypic/Genomic Biomarkers. Am J Transplant, 2016. 16(1): p. 221-34.
9. Leventhal, J. R., et al., Genomic biomarkers correlate with HLA-identical renal transplant tolerance. J Am Soc Nephrol, 2013. 24(9): p. 1376-85.
10. Scandling, J. D., et al., Tolerance and withdrawal of immunosuppressive drugs in patients given kidney and hematopoietic cell transplants. Am J Transplant, 2012. 12(5): p. 1133-45.
11. Scandling, J. D., et al., Chimerism, graft survival, and withdrawal of immunosuppressive drugs in HLA matched and mismatched patients after living donor kidney and hematopoietic cell transplantation. Am J Transplant, 2015. 15(3): p. 695-704.
12. Massart, A., et al., The DESCARTES-Nantes survey of kidney transplant recipients displaying clinical operational tolerance identifies 35 new tolerant patients and 34 almost tolerant patients. Nephrol Dial Transplant, 2016.
13. Roussey-Kesler, G., et al., Clinical operational tolerance after kidney transplantation. Am J Transplant, 2006. 6(4): p. 736-46.
14. Newell, K. A., et al., Identification of a B cell signature associated with renal transplant tolerance in humans. J Clin Invest, 2010. 120(6): p. 1836-47.

15. Sagoo, P., et al., Development of a cross-platform biomarker signature to detect renal transplant tolerance in humans. J Clin Invest, 2010. 120(6): p. 1848-61.
16. Hricik, D. E., et al., Adverse Outcomes of Tacrolimus Withdrawal in Immune-Quiescent Kidney Transplant Recipients. J Am Soc Nephrol, 2015.
17. Abramowicz, D., et al., Cyclosporine withdrawal from a mycophenolate mofetil-containing immunosuppressive regimen: results of a five-year, prospective, randomized study. J Am Soc Nephrol, 2005. 16(7): p. 2234-40.
18. Baron, D., et al., A common gene signature across multiple studies relate biomarkers and functional regulation in tolerance to renal allograft. Kidney Int, 2015. 87(5): p. 984-95.
19. Braudeau, C., et al., Variation in numbers of CD4+ CD25highFOXP3+ T cells with normal immuno-regulatory properties in long-term graft outcome. Transpl Int, 2007. 20(10): p. 845-55.
20. Braza, F., et al., Central Role of CD45RA− Foxp3hi Memory Regulatory T Cells in Clinical Kidney Transplantation Tolerance. J Am Soc Nephrol, 2015. 26(8): p. 1795-805.
21. Brouard, S., et al., Identification of a peripheral blood transcriptional biomarker panel associated with operational renal allograft tolerance. Proc Natl Acad Sci USA, 2007. 104(39): p. 15448-53.
22. Chesneau, M., et al., Tolerant Kidney Transplant Patients Produce B Cells with Regulatory Properties. J Am Soc Nephrol, 2015.
23. Danger, R., et al., Upregulation of miR-142-3p in peripheral blood mononuclear cells of operationally tolerant patients with a renal transplant. J Am Soc Nephrol, 2012. 23(4): p. 597-606.
24. Pallier, A., et al., Patients with drug-free long-term graft function display increased numbers of peripheral B cells with a memory and inhibitory phenotype. Kidney Int, 2010. 78(5): p. 503-13.
25. Silva, H. M., et al., Preserving the B-cell compartment favors operational tolerance in human renal transplantation. Mol Med, 2012. 18: p. 733-43.
26. Newell, K. A., et al., Longitudinal studies of a B cell-derived signature of tolerance in renal transplant recipients. Am J Transplant, 2015. 15(11): p. 2908-20.
27. Chesneau, M., et al., Unique B cell differentiation profile in tolerant kidney transplant patients. Am J Transplant, 2014. 14(1): p. 144-55.
28. Chesneau, M., et al., Tolerant kidney transplant patients produce B cells with regulatory properties. J Am Soc Nephrol, 2015. 26(10): p. 2588-98.
29. Deng, M. C., et al., Noninvasive discrimination of rejection in cardiac allograft recipients using gene expression profiling. Am J Transplant, 2006. 6(1): p. 150-60.
30. Mastoridis, S., M. Martinez-Llordella, and A. Sanchez-Fueyo, Biomarkers and immunopathology of tolerance. Curr Opin Organ Transplant, 2016. 21(1): p. 81-7.
31. Rohart, F., Multiple Hypotheses Testing For Variable Selection, 2011.
32. Biais, M., et al., Clinical relevance of pulse pressure variations for predicting fluid responsiveness in mechanically ventilated intensive care unit patients: the grey zone approach. Crit Care, 2014. 18(6): p. 587.
33. Roedder, S., et al., A three-gene assay for monitoring immune quiescence in kidney transplantation. J Am Soc Nephrol, 2015. 26(8): p. 2042-53.
34. Dell'Oglio, M. P., et al., The anti-fibrotic effect of mycophenolic acid-induced neutral endopeptidase. J Am Soc Nephrol, 2010. 21(12): p. 2157-68.
35. Brouard, S., et al., Comparative transcriptional and phenotypic peripheral blood analysis of kidney recipients under cyclosporin A or sirolimus monotherapy. Am J Transplant, 2010. 10(12): p. 2604-14.
36. Brouard, S., et al., The natural history of clinical operational tolerance after kidney transplantation through twenty-seven cases. Am J Transplant, 2012. 12(12): p. 3296-307.
37. Braza, F., J. P. Soulillou, and S. Brouard, Reconsidering the bio-detection of tolerance in renal transplantation. Chimerism, 2013. 4(1): p. 15-7.
38. Petrara, M. R., et al., Post-transplant lymphoproliferative disorders: from epidemiology to pathogenesis-driven treatment. Cancer Lett, 2015. 369(1): p. 37-44.
39. Everly, M. J., et al., Incidence and impact of de novo donor-specific alloantibody in primary renal allografts. Transplantation, 2013. 95(3): p. 410-7.
40. Brouard, S., et al., Identification of a gene expression profile associated with operational tolerance among a selected group of stable kidney transplant patients. Transpl Int, 2011. 24(6): p. 536-47.
41. Krepsova, E., et al., Effect of induction therapy on the expression of molecular markers associated with rejection and tolerance. BMC Nephrol, 2015. 16: p. 146.
42. Muller-Steinhardt, M., et al., The pharmacodynamic effect of sirolimus: individual variation of cytokine mRNA expression profiles in human whole blood samples. Immunobiology, 2009. 214(1): p. 17-26.
43. Roedder, S., et al., The kSORT assay to detect renal transplant patients at high risk for acute rejection: results of the multicenter AART study. PLoS Med, 2014. 11(11): p. e1001759.
44. Lee, A., et al., Validation study of peripheral blood diagnostic test for acute rejection in kidney transplantation. Transplantation, 2014. 98(7): p. 760-5.
45. Foucher, Y., et al., A clinical scoring system highly predictive of long-term kidney graft survival. Kidney Int, 2010. 78(12): p. 1288-94.
46. Lakkis, F. G. and M. H. Sayegh, Memory T cells: a hurdle to immunologic tolerance. J Am Soc Nephrol, 2003. 14(9): p. 2402-10.
47. Tullius, S. G., et al., The combination of donor and recipient age is critical in determining host immunoresponsiveness and renal transplant outcome. Ann Surg, 2010. 252(4): p. 662-74.
48. Benitez, C., et al., Prospective multicenter clinical trial of immunosuppressive drug withdrawal in stable adult liver transplant recipients. Hepatology, 2013. 58(5): p. 1824-35.
49. Heidt, S., et al., B cell markers of operational tolerance can discriminate acute kidney allograft rejection from stable graft function. Transplantation, 2014.
50. Braud, C., et al., Immunosuppressive drug-free operational immune tolerance in human kidney transplant recipients: Part I. Blood gene expression statistical analysis. J Cell Biochem, 2008. 103(6): p. 1681-92.
51. Lozano, J. J., et al., Comparison of transcriptional and blood cell-phenotypic markers between operationally tolerant liver and kidney recipients. Am J Transplant, 2011. 11(9): p. 1916-26.
52. Gautier, L., et al., affy—analysis of Affymetrix GeneChip data at the probe level. Bioinformatics, 2004. 20(3): p. 307-15.
53. PE Applied Biosystems, F. C., ABI PRISM 7900 user bulletin, 1997. 2: p. 11-24.

The invention claimed is:

1. A method of treating a transplanted human kidney recipient with an immunosuppressive therapy comprising the steps of:
   i) determining whether the human kidney recipient is an operationally tolerant (TOL) human kidney recipient or a non-operationally tolerant (STA) human kidney recipient by:
      a. establishing a composite score of tolerance (cSoT) with the expression levels of six genes in a biological sample obtained from said human kidney recipient and two clinical parameters;
         wherein said six genes are ID3, AKR1C3, CD40, CTLA4, TCL1A and MZB1;
         wherein said two clinical parameters are age of the human kidney recipient at test time and age of the human kidney recipient at transplantation time;
         wherein said cSoT is established by the following formula:

$$cSoT = \sum_{i}^{n} = \beta_i \times Exprs + \beta_{test\ time} \times age_{test\ time} + \beta_{trans\ time} \times age_{trans\ time} + \text{intercept} - \text{scaling coefficient}$$

and wherein:
   $\beta_i$ is a regression coefficient of each gene,
   Exprs is expression level of each gene,
   $\beta_{test\ time}$ is a regression coefficient of the age of the human kidney recipient at the test time,
   $age_{test\ time}$ is the age of the human kidney recipient at the test time,
   $\beta_{trans\ time}$ is a regression coefficient of the age of the human kidney recipient at the transplantation time,
   $age_{trans\ time}$ is the age of the human kidney recipient at the transplantation time, and
   intercept is interception of the regression curve to the Y axis;
      b. comparing this cSoT with a predetermined reference value; and
      c. concluding that the human kidney recipient is TOL when the cSoT is higher than the predetermined reference value or concluding that the human kidney recipient is STA when the cSoT is lower than the predetermined reference value; and
   ii) treating the human kidney recipient with immunosuppressive therapy when the human kidney recipient is STA.

2. The method according to claim 1, wherein the predetermined reference value is the cSoT of a TOL human kidney recipient.

3. The method according to claim 1, wherein the predetermined reference value is the cSoT of a STA human kidney recipient.

4. The method according to claim 1, wherein said human kidney recipient has further been grafted with the pancreas, and optionally a piece of duodenum, of the kidney donor.

5. The method according to claim 1, wherein said immunosuppressive therapy is selected from the group consisting of azathioprine, methotrexate, cyclophosphamide, tacrolimus, sirolimus, everolimus, rapamycin, corticosteroids, cyclosporins, mycophenolic acid, leflumacide, ascomycin, hydroxyurea, and combinations thereof.

6. A method for identifying a transplanted human kidney recipient under immunosuppressive therapy as a candidate for immunosuppressive therapy weaning or minimization, comprising the steps of:
   i) determining whether the human kidney recipient is an operationally tolerant (TOL) human kidney recipient or a non-operationally tolerant (STA) human kidney recipient by:
      a. establishing a composite score of tolerance (cSoT) with the expression levels of six genes in a biological sample obtained from said human kidney recipient and two clinical parameters;
         wherein said six genes are ID3, AKR1C3, CD40, CTLA4, TCL1A and MZB1;
         wherein said two clinical parameters are the age of the human kidney recipient at test time and the age of the human kidney recipient at transplantation time;
         wherein said cSoT is established by the following formula:

$$cSoT = \sum_{i}^{n} = \beta_i \times Exprs + \beta_{test\ time} \times age_{test\ time} + \beta_{trans\ time} \times age_{trans\ time} + \text{intercept} - \text{scaling coefficient}$$

and wherein:
   $\beta_i$ is a regression coefficient of each gene,
   Exprs is expression level of each gene,
   $\beta_{test\ time}$ is a regression coefficient of the age of the human kidney recipient at the test time,
   $age_{test\ time}$ is the age of the human kidney recipient at the test time,
   $\beta_{trans\ time}$ is a regression coefficient of the age of the human kidney recipient at the transplantation time,
   $age_{trans\ time}$ is the age of the human kidney recipient at the transplantation time, and
   intercept is interception of the regression curve to the Y axis;
      b. comparing this cSoT with a predetermined reference value; and
      c. concluding that the human kidney recipient is TOL when the cSoT is higher than the predetermined reference value or concluding that the human kidney recipient is STA when the cSoT is lower than the predetermined reference value; and
   ii) reducing or suppressing the immunosuppressive therapy when the human kidney recipient is TOL.

7. The method according to claim 6, wherein the predetermined reference value is the cSoT of a TOL human kidney recipient.

8. The method according to claim 6, wherein the predetermined reference value is the cSoT of a STA human kidney recipient.

9. The method according to claim 6, wherein said human kidney recipient has further been grafted with the pancreas, and optionally a piece of duodenum, of the kidney donor.

10. The method according to claim 6, wherein said immunosuppressive therapy is selected from the group consisting of azathioprine, methotrexate, cyclophosphamide, tacrolimus, sirolimus, everolimus, rapamycin, corticosteroids, cyclosporins, mycophenolic acid, leflumacide, ascomycin, hydroxyurea, and combinations thereof.

* * * * *